(12) United States Patent
Wang et al.

(10) Patent No.: US 10,973,671 B2
(45) Date of Patent: Apr. 13, 2021

(54) FOOT ASSISTIVE DEVICE FOR IMPROVING DROP FOOT GAIT

(71) Applicant: YONG TAI GLOBAL CO., LTD., Tainan (TW)

(72) Inventors: Tseng-Chiu Wang, Tainan (TW); Hung-Chi Wang, Tainan (TW)

(73) Assignee: Yong Tai Global Co., Ltd., Tainan (TW)

( * ) Notice: Subject to any disclaimer, the term of this patent is extended or adjusted under 35 U.S.C. 154(b) by 322 days.

(21) Appl. No.: 16/021,459

(22) Filed: Jun. 28, 2018

(65) Prior Publication Data

US 2019/0142621 A1 May 16, 2019

(30) Foreign Application Priority Data

Nov. 10, 2017 (TW) .................................. 106216791

(51) Int. Cl.
*A61F 5/01* (2006.01)

(52) U.S. Cl.
CPC .... *A61F 5/0127* (2013.01); *A61F 2005/0167* (2013.01); *A61F 2005/0172* (2013.01); *A61F 2005/0179* (2013.01)

(58) Field of Classification Search
CPC .... A61F 5/0111; A61F 5/0123; A61F 5/0125; A61F 5/0113; A61F 5/0127; A61F 5/0179; A61F 2005/0132; A61F 2005/0165; A61F 2005/0167; A61F 2005/0179; A61F 2005/0158; A61F 2005/0197
See application file for complete search history.

(56) References Cited

U.S. PATENT DOCUMENTS

| 2,557,603 | A | * | 6/1951 | Invidiato | A61F 5/0127 602/28 |
| 2,663,294 | A | * | 12/1953 | Harrison | A61F 5/0113 602/28 |
| 3,826,251 | A | * | 7/1974 | Ross | A61F 2/646 602/16 |
| 4,938,777 | A | * | 7/1990 | Mason | A61F 5/0113 602/27 |
| 5,328,444 | A | * | 7/1994 | Whiteside | A61F 5/0127 16/375 |
| 6,171,272 | B1 | * | 1/2001 | Akita | A61F 5/0127 602/27 |
| 6,993,808 | B1 | * | 2/2006 | Bennett | A61F 5/0125 16/321 |

(Continued)

FOREIGN PATENT DOCUMENTS

TW 526752 4/2003

*Primary Examiner* — Alireza Nia
*Assistant Examiner* — Kevin S Albers
(74) *Attorney, Agent, or Firm* — Rosenberg, Klein & Lee

(57) ABSTRACT

A foot assistive device for improving drop foot gait comprises an assistive device body and an elastic module. The assistive device body comprises a foot support base and a brace. The foot support base is movably connected to the brace. The elastic module connects the foot support base to the brace. The elastic module has a spring, a preset support included angle is formed between the foot support base and the brace under an elastic force of the spring. The support included angle is not larger than 90°. Thereby, when the foot is raised up, the foot support base is unlikely to drop excessively due to the foot weight, the drop foot gait is improved effectively.

11 Claims, 17 Drawing Sheets

(56) References Cited

U.S. PATENT DOCUMENTS

| | | | |
|---|---|---|---|
| 7,682,322 B2 | 3/2010 | Engelman | |
| 2008/0269656 A1* | 10/2008 | Arnold | A61F 5/0195 |
| | | | 602/28 |
| 2009/0326426 A1* | 12/2009 | DeToro | A61F 5/0127 |
| | | | 602/16 |
| 2011/0040225 A1* | 2/2011 | Gibbons | A63B 21/00072 |
| | | | 602/23 |
| 2015/0141893 A1* | 5/2015 | Grosland | A61F 5/0193 |
| | | | 602/29 |

* cited by examiner

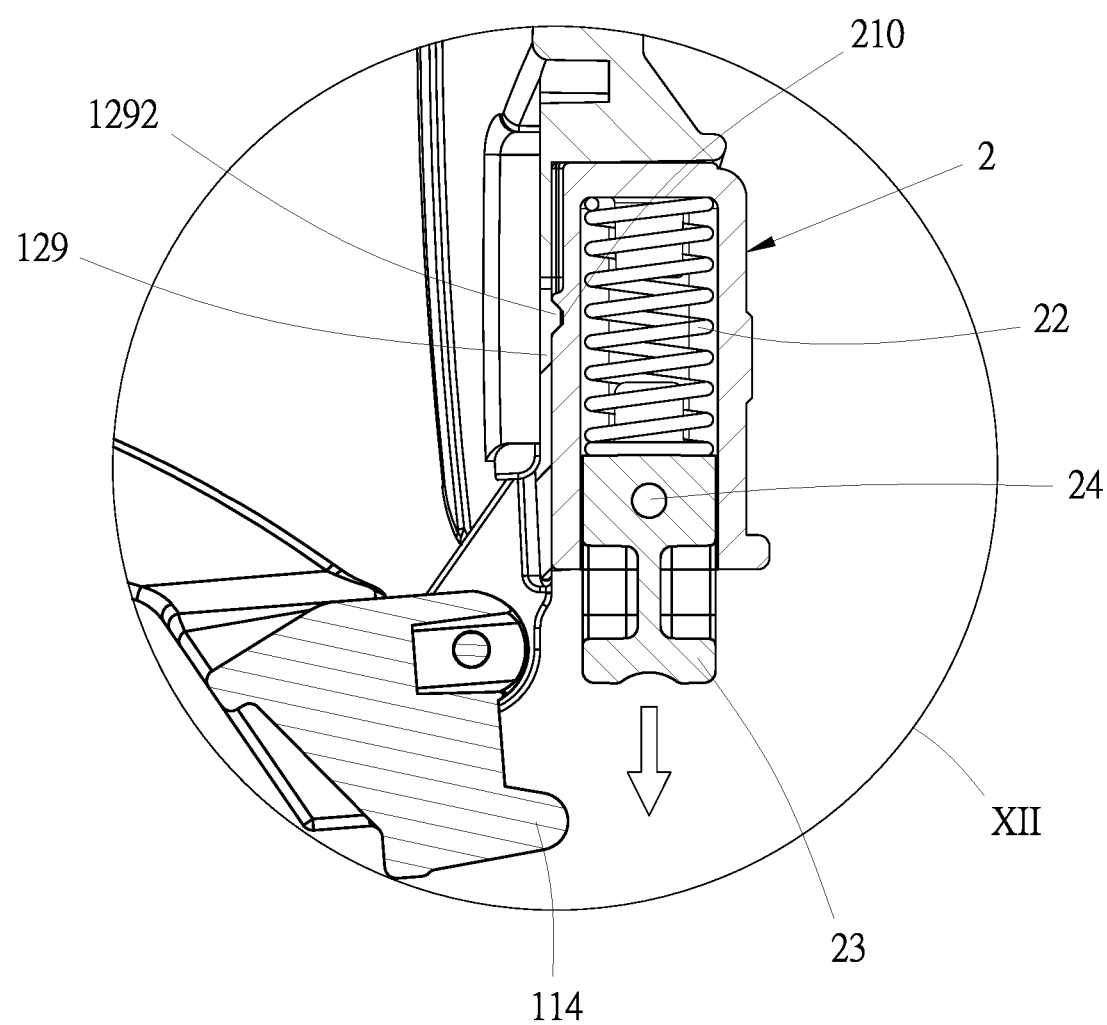
F I G . 12

FOOT ASSISTIVE DEVICE FOR IMPROVING DROP FOOT GAIT

BACKGROUND OF INVENTION

1. Field of the Invention

The present invention relates generally to a foot assistive device, and more particularly to a foot assistive device for improving drop foot gait.

2. Description of Related Art

The drop foot is a clinical phenomenon, its formal name is equinus foot. Because of central nerve injury or leg fracture, the ankle is unable or hard to perform dorsiflexion, leading to the drop foot phenomenon. The drop foot phenomenon leads to compensatory gaits of the patient, such as raising pelvis to avoid dragging foot on the ground, using hip and knee more by steppage gait to prolong the foot lift-off time. Said compensatory gaits will consume more muscle strength of the patient in walking on the one hand, on the other hand the patient is likely to fall down, affecting the walking safety.

At present, some suppliers have developed foot assistive devices to improve said drop foot gait. The previous cases include the "structure of foot board orthopedic shoe" of Taiwan utility patent bulletin No. 526752, which comprises a horizontal part for fixing the foot and a vertical part for fixing the lower limb, the horizontal part is connected to the vertical part by a connecting device with flexibility and elasticity, so as to improve the drop foot patient's drop foot condition. However, the structure of this previous case uses vertically connected horizontal part and vertical part, when the patient's foot is raised up, the horizontal part still may drop due to the foot weight, it is difficult to improve the drop foot problem effectively. Secondly, the connecting device is made of strip-shaped plastic material with elasticity and flexibility, this connecting device is not a general part, it is inconvenient to be changed.

SUMMARY OF THE INVENTION

In order to improve the drop foot gait more effectively by foot assistive device, this inventor proposes a foot assistive device for improving drop foot gait, which comprises an assistive device body and an elastic module. The assistive device body comprises a foot support base and a brace. The foot support base is movably connected to the brace. The elastic module connects the foot support base to the brace. The elastic module has a spring, an elastic force of the spring results in a preset support included angle between the foot support base and the brace. The support included angle is not larger than 90°.

Furthermore, the foot support base and the brace have a pivot joint part respectively. The pivot joint part of the foot support base is pivoted on the pivot joint part of the brace.

Furthermore, the brace has an elastic module mounting part, the elastic module mounting part is located near the pivot joint part of the brace. The elastic module is removably installed on the elastic module mounting part.

Furthermore, the elastic module has a casing holder, the spring is contained in a holding space of the casing holder. One of the casing holder and the elastic module mounting part has a snap, the other one of the casing holder and the elastic module mounting part has a clamping hole. The snap removably engages with the clamping hole.

Furthermore, the casing holder has an opening, the opening is connected to the holding space. The elastic module has a push-prop piece. The push-prop piece is movably connected to the casing holder and located at the opening. The spring props the push-prop piece, so that the push-prop piece props a propping part of the foot support base.

Furthermore, the casing holder has an elongated slot; the elastic module has a latch through the elongated slot and the push-prop piece to limit a displacement travel of the push-prop piece.

Furthermore, the foot support base has a hollow heel restraining part. The heel restraining part is located near the pivot joint part of the foot support base.

Furthermore, the foot support base has two first bandage connecting parts, a second bandage connecting part and a third bandage connecting part. Said two first bandage connecting parts are opposite to each other, and said two first bandage connecting parts are located near a front end of the foot support base. The second bandage connecting part is located near a back end of the foot support base. The third bandage connecting part is located between the second bandage connecting part and the back end, and the third bandage connecting part is relatively higher than the second bandage connecting part.

Furthermore, the brace has two fourth bandage connecting parts. Said two fourth bandage connecting parts are opposite to each other, and said two fourth bandage connecting parts are located near a top of the brace.

Furthermore, a leg contact side of the brace is provided with a soft protection pad.

Furthermore, the brace has an elastic module mounting part. The elastic module mounting part is located near the pivot joint part of the brace. The elastic module comprises a casing holder, a plurality of springs and a plurality of push-prop pieces. The casing holder is rotatably pivoted on the elastic module mounting part through a pivot. The casing holder is centered on the pivot and surrounded with a plurality of holding chambers. Each of said holding chambers is provided with one of said springs and one of said push-prop pieces. When the casing holder is rotated, one of said push-prop pieces props a propping part of the foot support base.

Furthermore, one of the elastic module mounting part and the casing holder has at least one snap, the other one of the casing holder and the elastic module mounting part has at least one clamping hole. The snap removably engages with the clamping hole.

Furthermore, a plurality of said snaps and said clamping holes are distributed annularly and centered on the pivot.

The following effects can be obtained according to said technical characteristics:

1. As the support included angle between the foot support base and brace is not larger than 90°, when the foot is raised up, the foot support base is unlikely to drop excessively due to the foot weight, the drop foot gait is improved effectively.

2. The springs used are common and normalized, easy to obtain and change.

3. The foot support base and brace can be connected by pivot, stretching displacement stably.

4. The elastic module is modular and detachable, it can be replaced by the elastic module of the required elastic force rapidly and conveniently, so as to further enhance the convenience of product part replacement.

5. The elastic module and elastic module mounting part of brace can be engaged by snap, implementing positioning effect and disassembly/assembly convenience.

6. The spring is mounted in the casing holder, so it is unlikely to be damaged by external environment factors.

7. The foot support base has a heel restraining part to avoid the user falling down due to foot slip, the wearing stability is enhanced, so as to enhance the walking safety.

8. The foot support base can be fixed by bandage at instep and ankle, so as to fix the foot more effectively.

9. The brace can be provided with a soft protection pad to enhance the wear comfort.

10. The elastic module is rotatable and provided with multiple springs for the user to choose appropriate spring as required.

11. The rotation position of elastic module can be located by snap, so as to implement positioning effect and switchover convenience.

BRIEF DESCRIPTION OF THE DRAWINGS

FIG. 12 is the close-up view of FIG. 11.

DETAILED DESCRIPTION OF THE INVENTION

To sum up the technical characteristics, the main effects of the foot assistive device for improving drop foot gait of the present invention will be clarified in the following embodiments.

Figure 1:
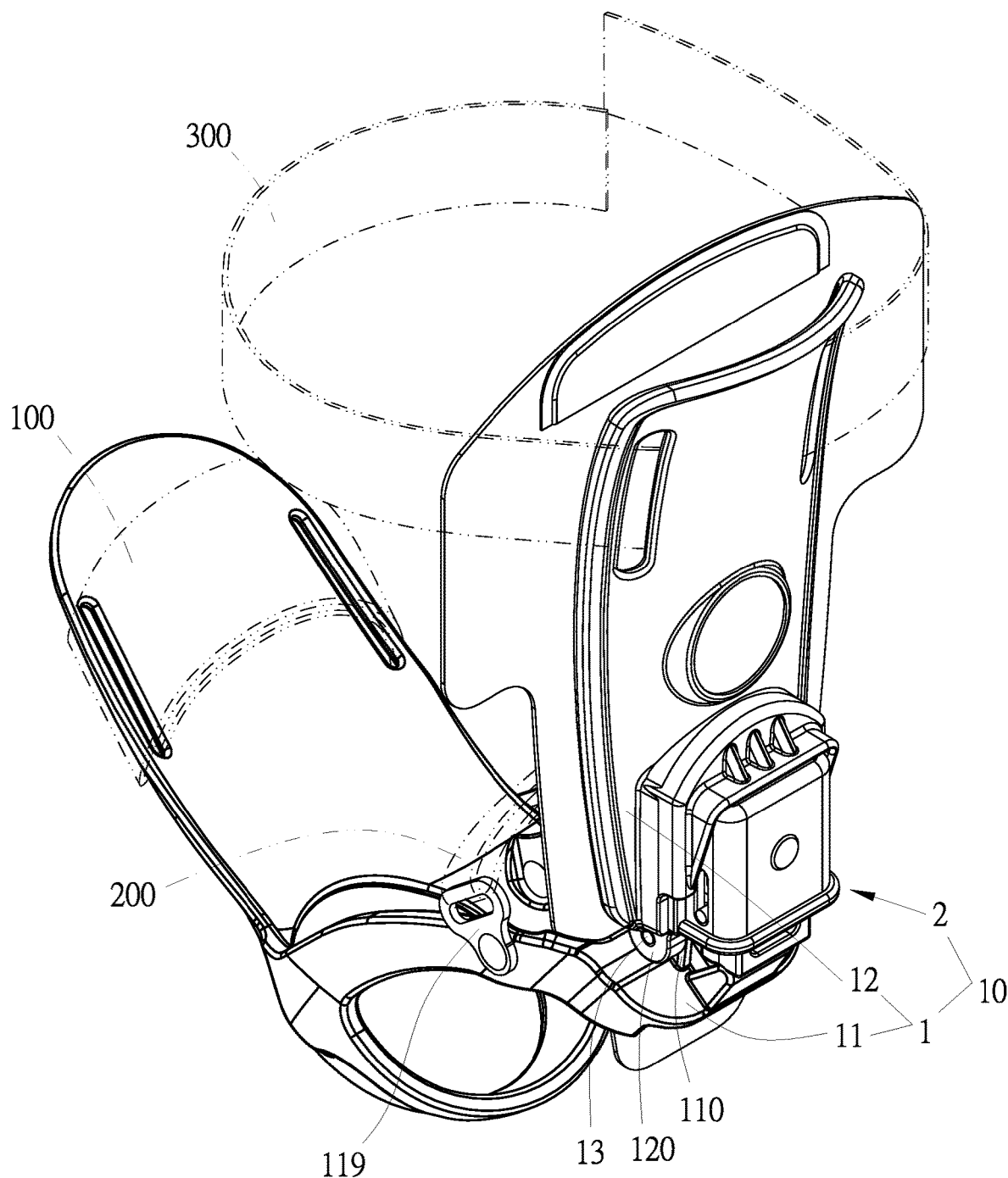
FIG. 1 is the three-dimensional outside view of embodiment of the present invention.

FIG. 1 discloses the foot assistive device for improving drop foot gait (10) of embodiment of the present invention, comprising an assistive device body (1) and an elastic module (2). The assistive device body (1) comprises a foot support base (11) and a brace (12). The foot support base (11) is movably connected to the brace (12). For example, the foot support base (11) and the brace (12) have a pivot joint part (110) (120) corresponding to each other. The pivot joint part (110) of the foot support base (11) can be pivoted on the pivot joint part (120) of the brace (12) by a pivot (13), so that the foot support base (11) and the brace (12) can pivot on each other. The elastic module (2) connects the foot support base (11) to the brace (12), so that the foot support base (11) and the brace (12) are located in the default relative positions under the effect of the elastic module (2).

Figure 2:
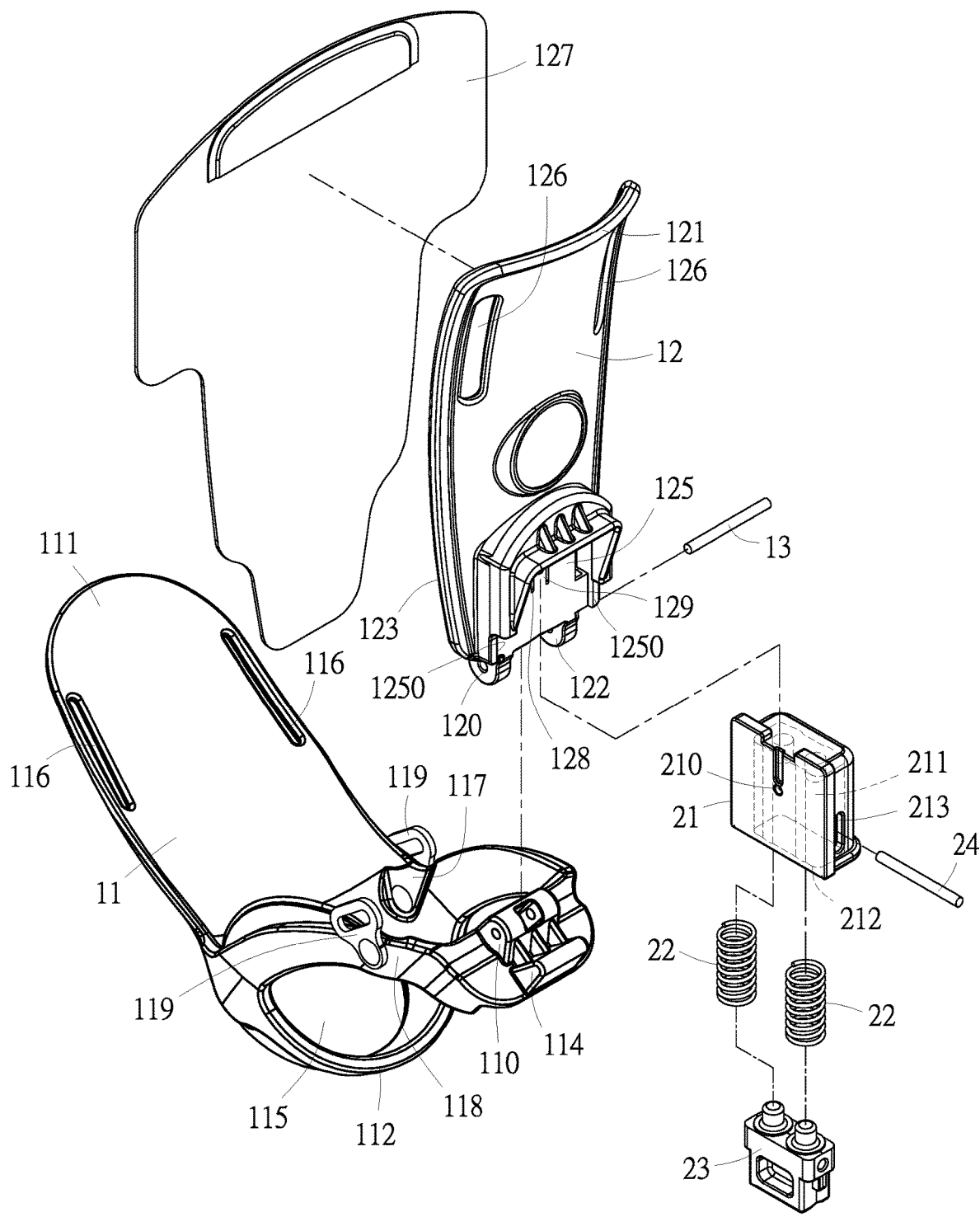
FIG. 2 is the three-dimensional exploded view of embodiment of the present invention.

Referring to FIGS. 1 and 2, the foot support base (11) form can be designed according to the foot anatomy principle, supporting the sole and instep, and can be designed in universal size applicable to most shoes. In addition, the foot support base (11) can deviate an angle outwards in relation to the brace (12) (e.g. 10°, so as to correspond to the spontaneously splay angle of tiptoe). The foot support base (11) has a front end (111) and a back end (112). Said pivot joint part (110) and a propping part (114) extend upwards near the back end (112). The propping part (114) is lug shaped and located near the pivot joint part (110). The foot support base (11) can have a hollow heel restraining part (115). The heel restraining part (115) is located near the back end (112).

In this embodiment, the foot support base (11) has two first bandage connecting parts (116), a second bandage connecting part (117) and a third bandage connecting part (118). Said two first bandage connecting parts (116) are punch holes opposite to each other, and said two first bandage connecting parts (116) are located near the front end (111) of the foot support base (11). Said two first bandage connecting parts (116) are connected by a first bandage (100) (e.g. Velcro), so as to fix the instep. The second bandage connecting part (117) is located near the back end (112) of the foot support base (11). The third bandage connecting part (118) is located between the second bandage connecting part (117) and the back end (112), and the location of the third bandage connecting part (118) is relatively higher than the second bandage connecting part (117). The second bandage connecting part (117) and the third bandage connecting part (118) are connected by a second bandage (200) (e.g. Velcro). The second bandage (200) fixes the ankle. In this embodiment, the second bandage connecting part (117) and the third bandage connecting part (118) can be pivoted on a connection strap (119), and then the two connection straps (119) are connected to the second bandage (200), so as to fit different ankle sizes.

The brace (12) has a top (121), a bottom (122) and a leg contact side (123). The brace (12) has an elastic module mounting part (125) near the bottom (122) and the pivot joint part (120). Preferably, the brace (12) has two fourth bandage connecting parts (126) near the top (121). Said two fourth bandage connecting parts (126) are opposite to each other for a third bandage (300) to connect said two fourth bandage connecting parts (126) (e.g. Velcro), so as to fix the leg. In this embodiment, the leg contact side (123) of the brace (12) can be provided with a soft protection pad (127). The soft protection pad (127) can absorb moisture and drain off sweat, so as to enhance the wear comfort.

Figure 3:
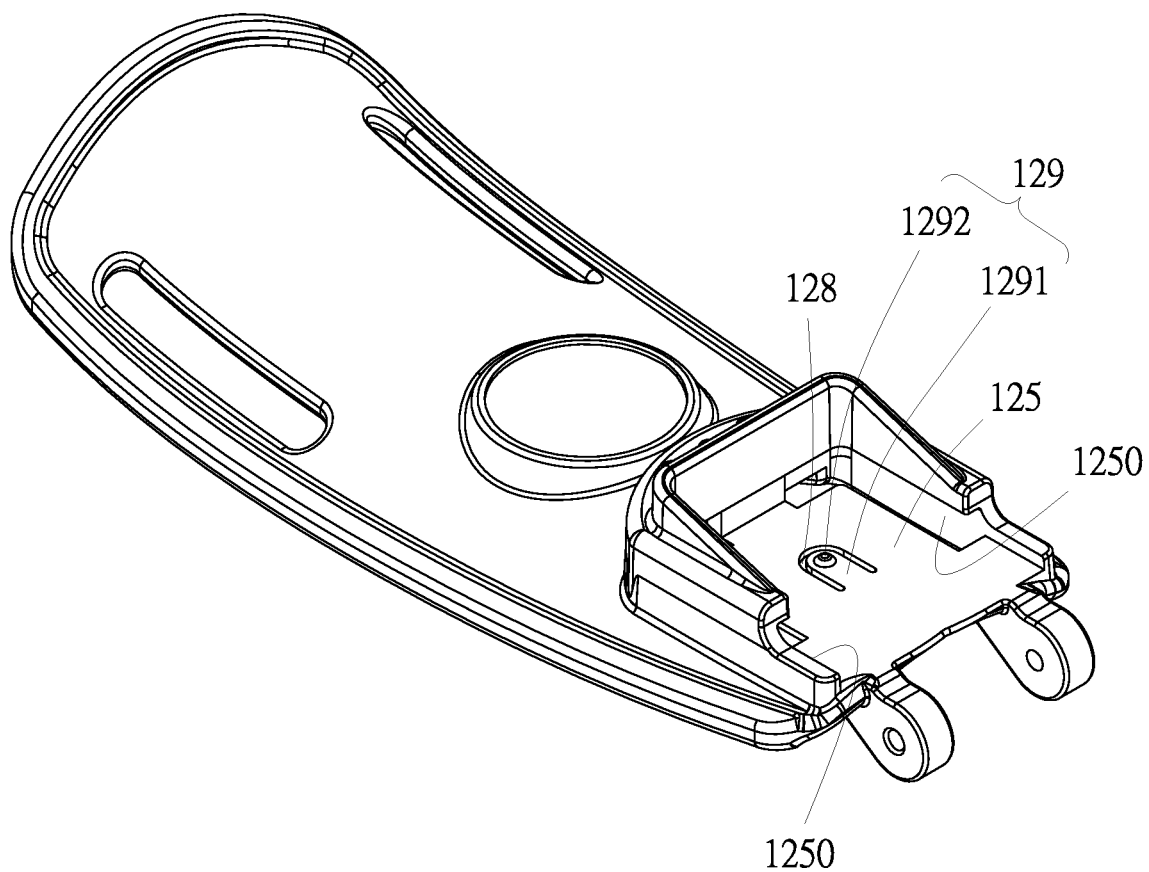
FIG. 3 is the three-dimensional outside view of foot support base in the embodiment of the present invention.
Figure 4:
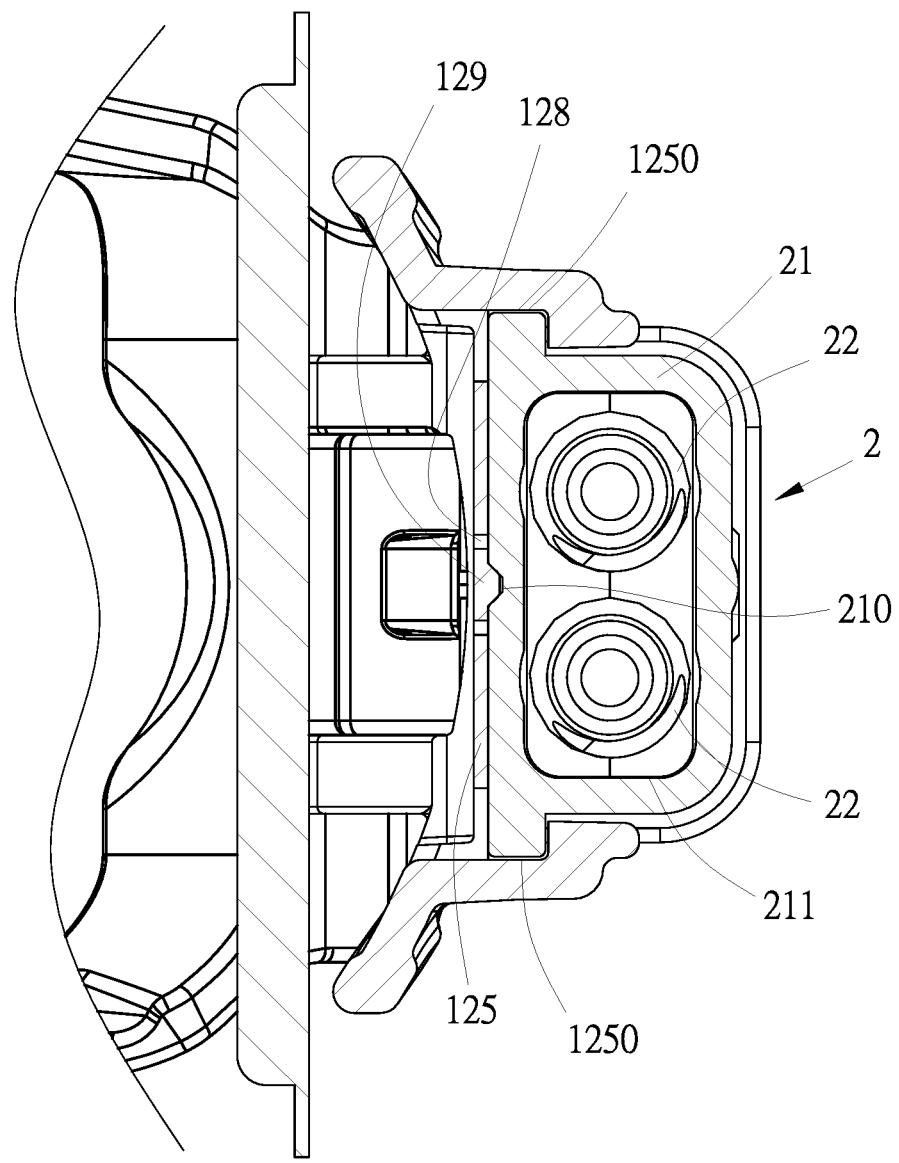
FIG. 4 is the combined section view of elastic module mounting part and elastic module in the embodiment of the present invention.

As shown in FIG. 2 and FIG. 3, the elastic module (2) is removably installed on the elastic module mounting part (125). To be specific, one of a casing holder (21) of the elastic module (2) and the elastic module mounting part (125) has a snap, the other one of the casing holder (21) and the elastic module mounting part (125) has a clamping hole for the snap to engage removably. In this embodiment, the elastic module mounting part (125) can have a U-shaped slot (128), and a snap (129) is formed in the U-shaped slot (128)

by a cantilevered member (1291) having a projection (1292) at its distal end, the clamping hole (210) can be located in the casing holder (21). As shown in FIG. 3 and FIG. 4, the elastic module mounting part (125) can have a pair of guide parts (1250), so as to guide the casing holder (21) preferably, the clamping hole (210) of the casing holder (21) clamps the snap (129) by receiving the projection (1292) therein. The locations of said clamping hole (210) and snap (129) can be interchanged, not limited to the pattern of this embodiment.

Figure 5:
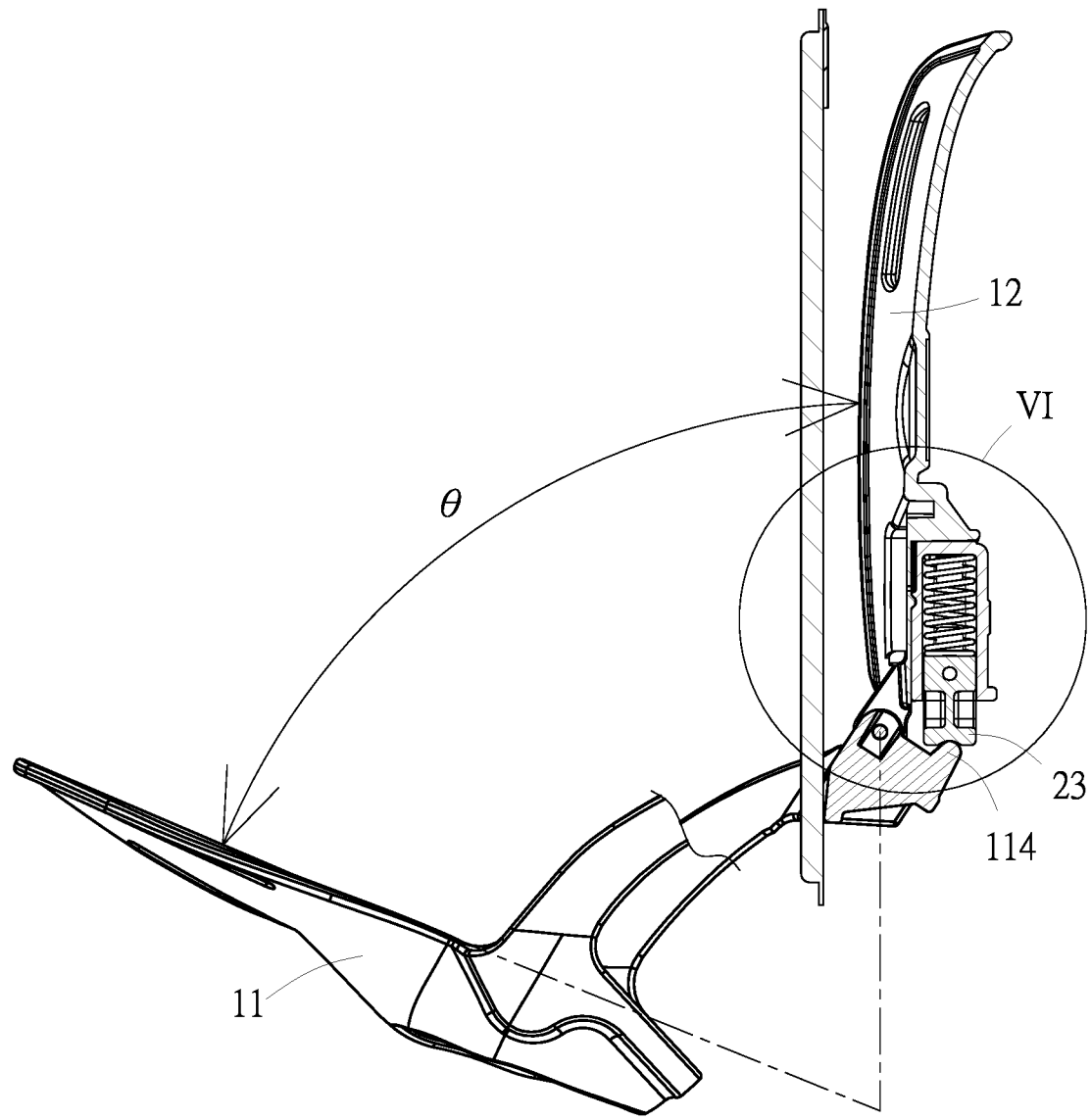
FIG. 5 is the side view and partial section view of the embodiment of the present invention before use.
Figure 6:
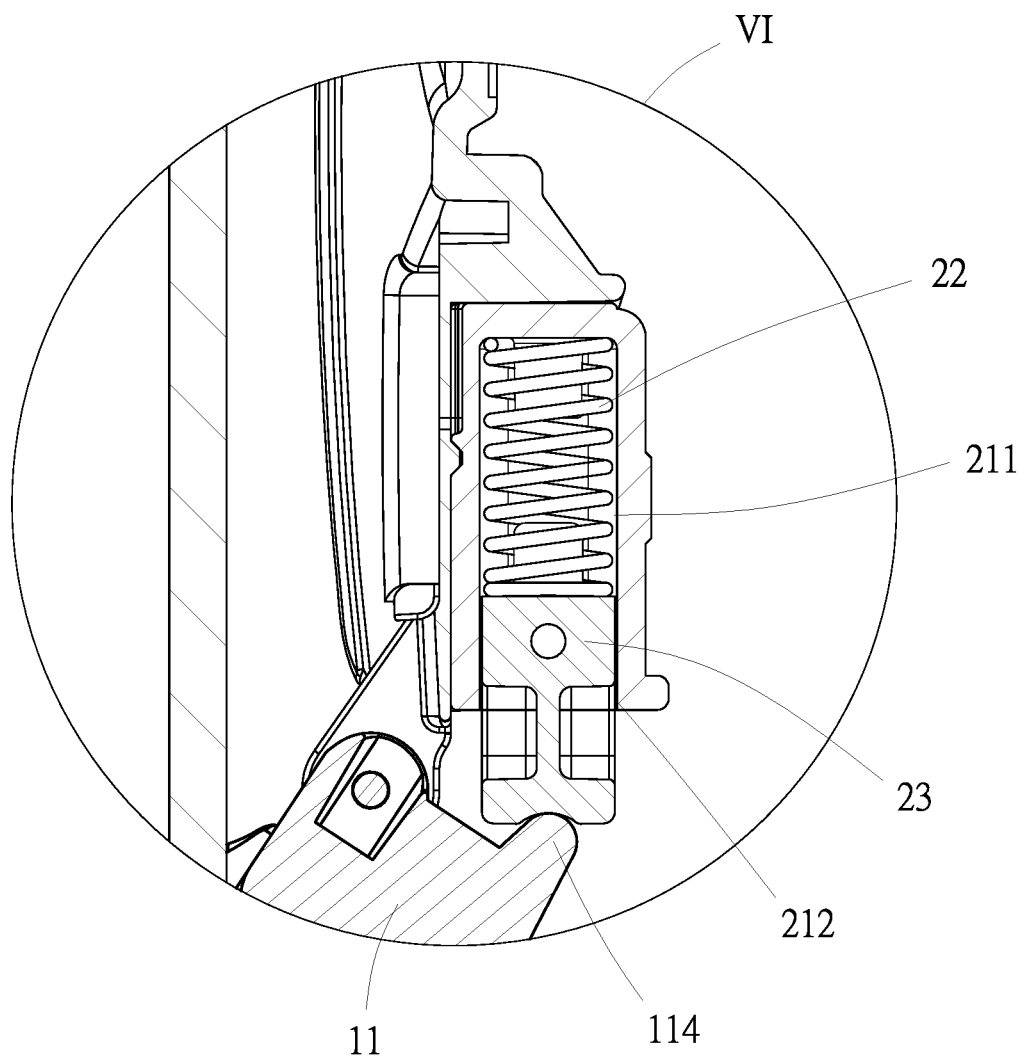
FIG. 6 is the close-up view of FIG. 5.

As shown in FIG. 2, the casing holder (21) defines a holding space (211) and an opening (212). The opening (212) is connected to the holding space (211). The elastic module (2) has a plurality of springs (22) and a push-prop piece (23). The casing holder (21) has an elongated slot (213). The elastic module (2) has a latch (24). The latch (24) can penetrate through the elongated slot (213) and the push-prop piece (23), so as to limit a displacement travel of the push-prop piece (23). As shown in FIG. 5 and FIG. 6, said springs (22) are contained in the holding space (211) of the casing holder (21). The push-prop piece (23) is movably connected to the casing holder (21) and located at the opening (212). The springs (22) prop the push-prop piece (23), so that the push-prop piece (23) can prop the propping part (114) of the foot support base (11), and a support included angle (θ) preset not larger than 90° is formed between the foot support base (11) and the brace (12).

Figure 7:
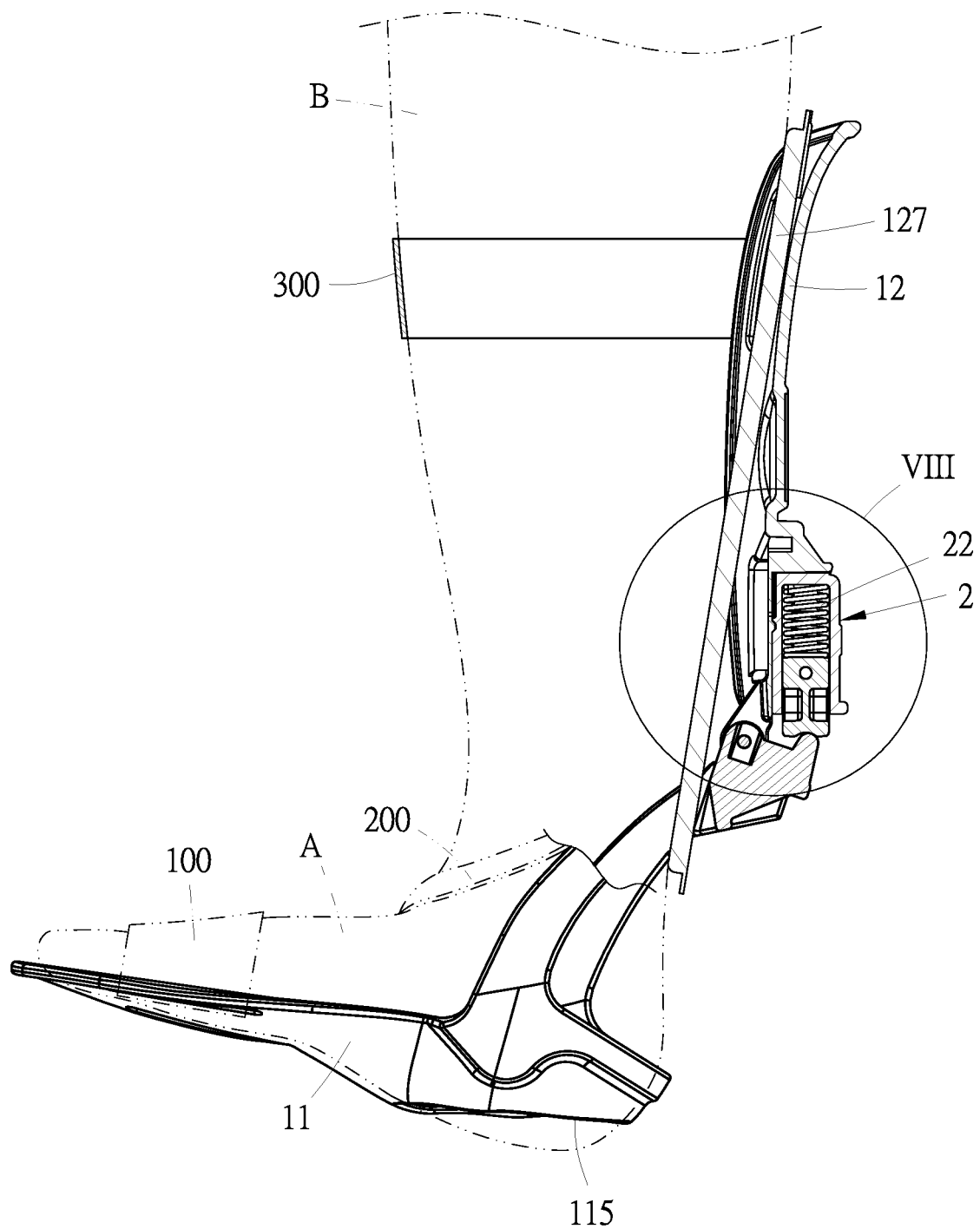
FIG. 7 is the side view and partial section view of the embodiment of the present invention when the foot is raised.
Figure 8:
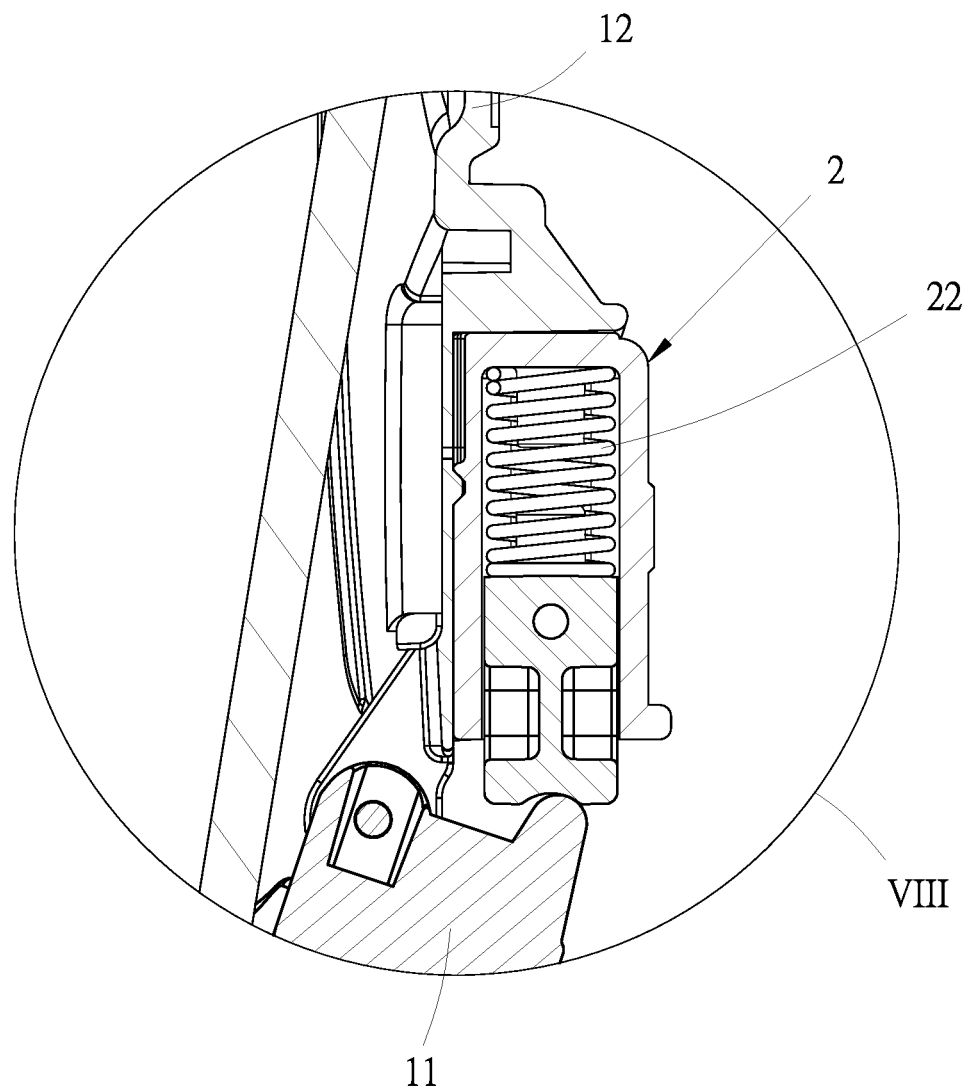
FIG. 8 is the close-up view of FIG. 7.
Figure 9:
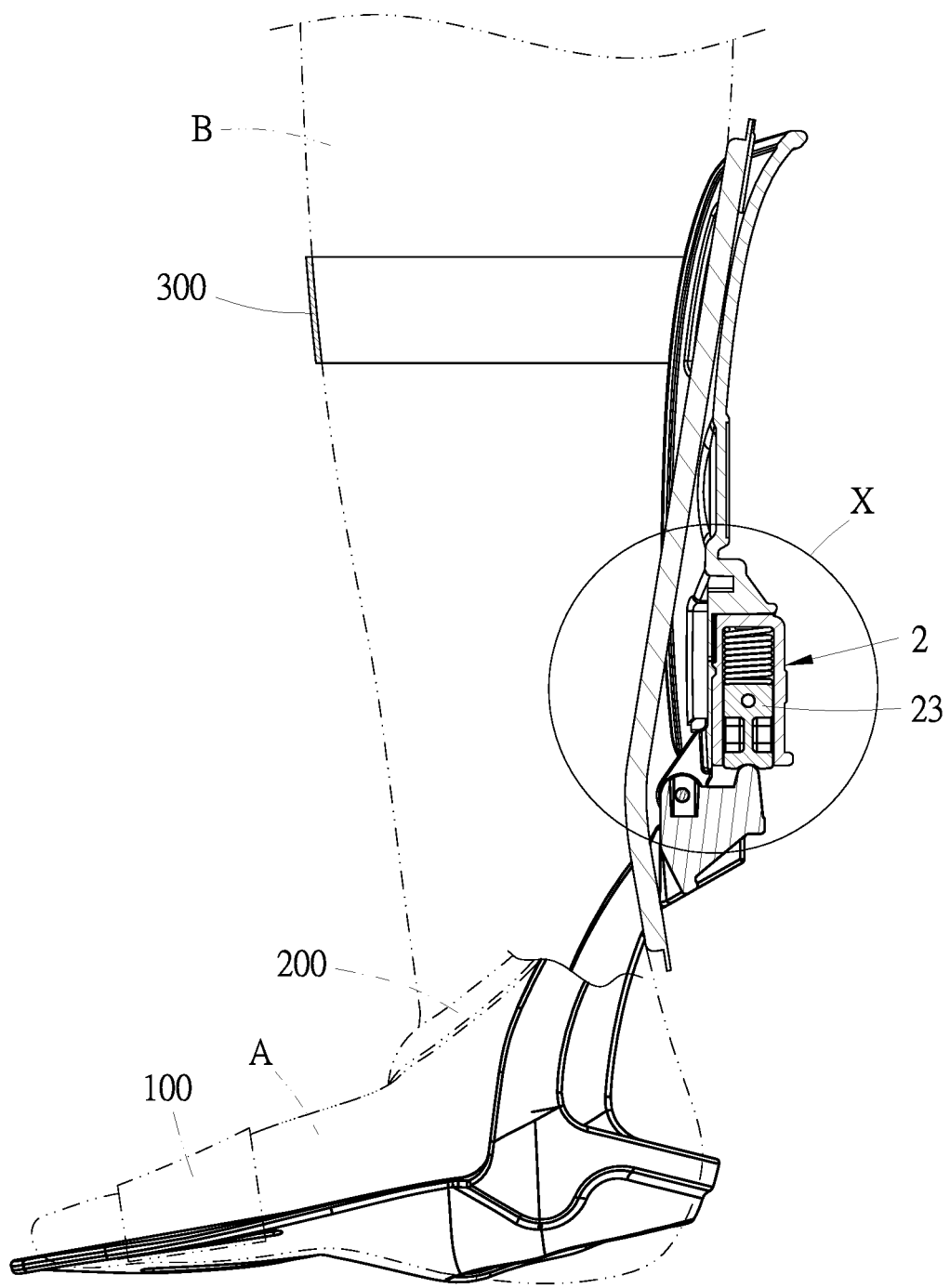
FIG. 9 is the side view and partial section view of the embodiment of the present invention in trampling mode.
Figure 10:
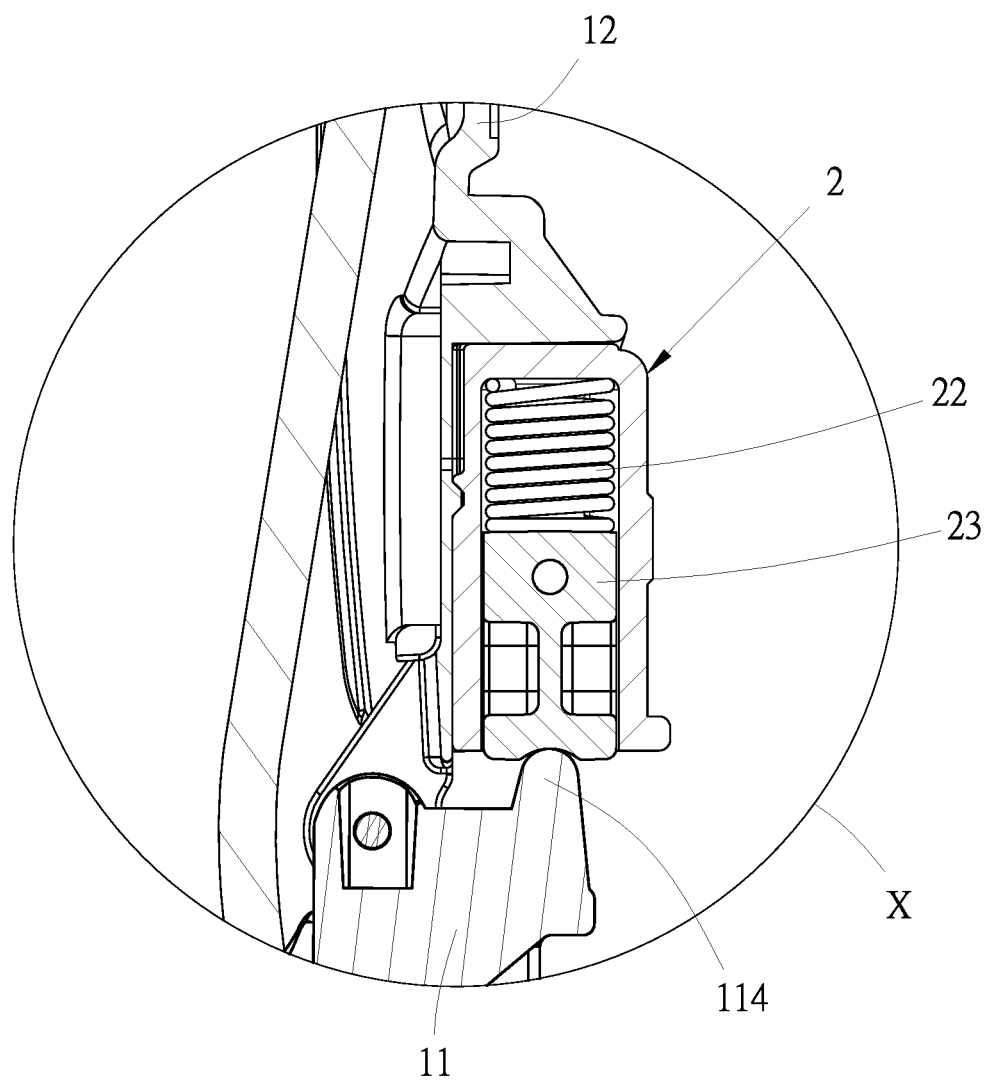
FIG. 10 is the close-up view of FIG. 9.

As shown in FIG. 7 and FIG. 8, when the foot assistive device (10) is put on the user's foot (A), the user's heel is aligned with hollow heel restraining part (115), so as to provide the restraining function and enhance the user's sole contact feedback, and the user's foot (A) can be fixed to the foot support base (11) by the first bandage (100) and the second bandage (200). The second bandage (200) can fix the talus, inhibit the drop foot abnormal tension of central nerve injury, and fix the ankle to the anatomically neutral position. The user's leg (B) is fixed to the brace (12) by the third bandage (300). When the user's foot (A) is raised up, the muscles of ankle can perform dorsiflexion under the elastic force of springs (22), so as to avoid the user using compensatory gaits, meeting the human engineering of normal gait, so as to reduce the consumption of muscle strength, and to reduce the fall-down probability resulted from drop foot when the user is walking effectively. As shown in FIG. 9 and FIG. 10, when the user's foot (A) steps on the ground, under the muscle strength of stance, partial elastic force of said elastic module (2) will be overcome, so that the foot support base (11) pivots on the brace (12). Therefore, when the user is walking or stepping upstairs/downstairs, the gait will be actuated repeatedly as shown in FIG. 7 and FIG. 9.

Figure 11:
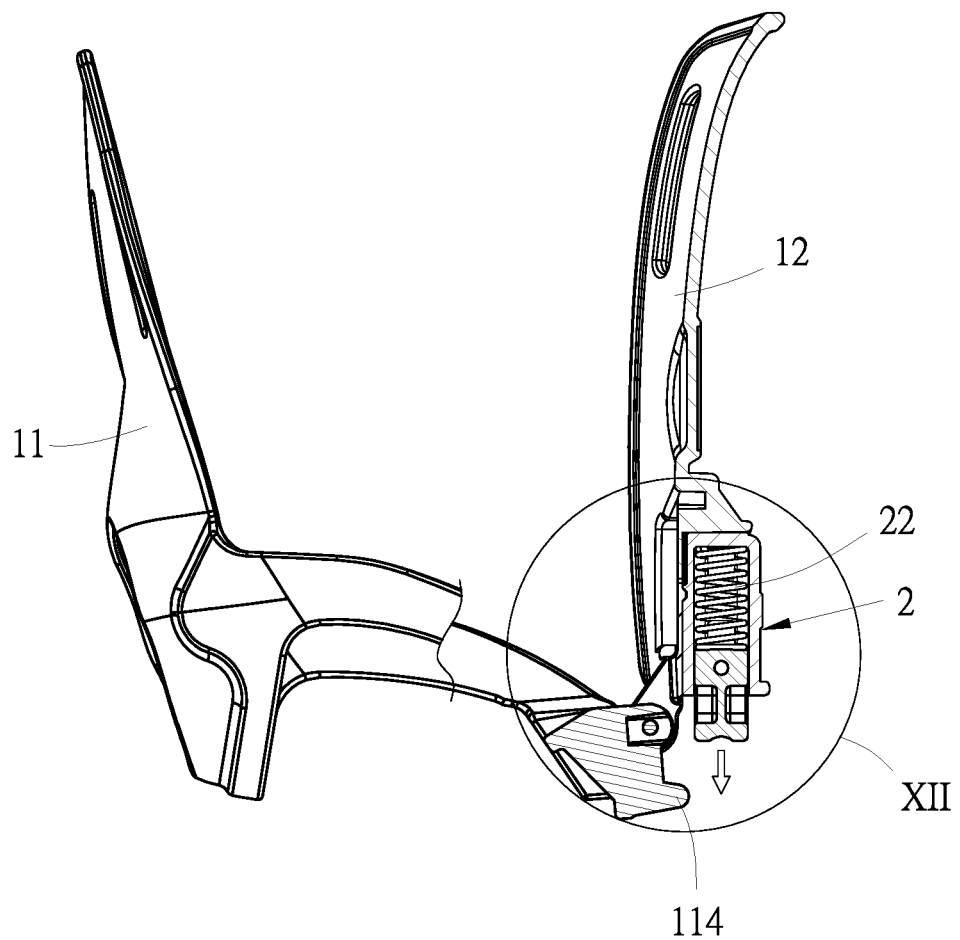
FIG. 11 is the side view and partial section view of the embodiment of the present invention before the elastic module is changed.

As shown in FIG. 11 and FIG. 12, when the elastic force of springs (22) is too strong or too weak, the user's gait mismatches normal gait or is uncomfortable, or when the springs (22) shall be changed, the foot support base (11) can pivot on the brace (12), so that the propping part (114) of the foot support base (11) departs from the push-prop piece (23) of said elastic module (2). Afterwards, the user can apply a force to draw out said elastic module (2), so that the clamping hole (210) of the elastic module (2) disengages the projection (1292) of the snap (129) to remove the brace (12). Thereby, the springs (22) of different E-moduli or a new elastic module (2) can be mounted, or the springs (22) can be changed by drawing out the latch (24).

Figure 13:
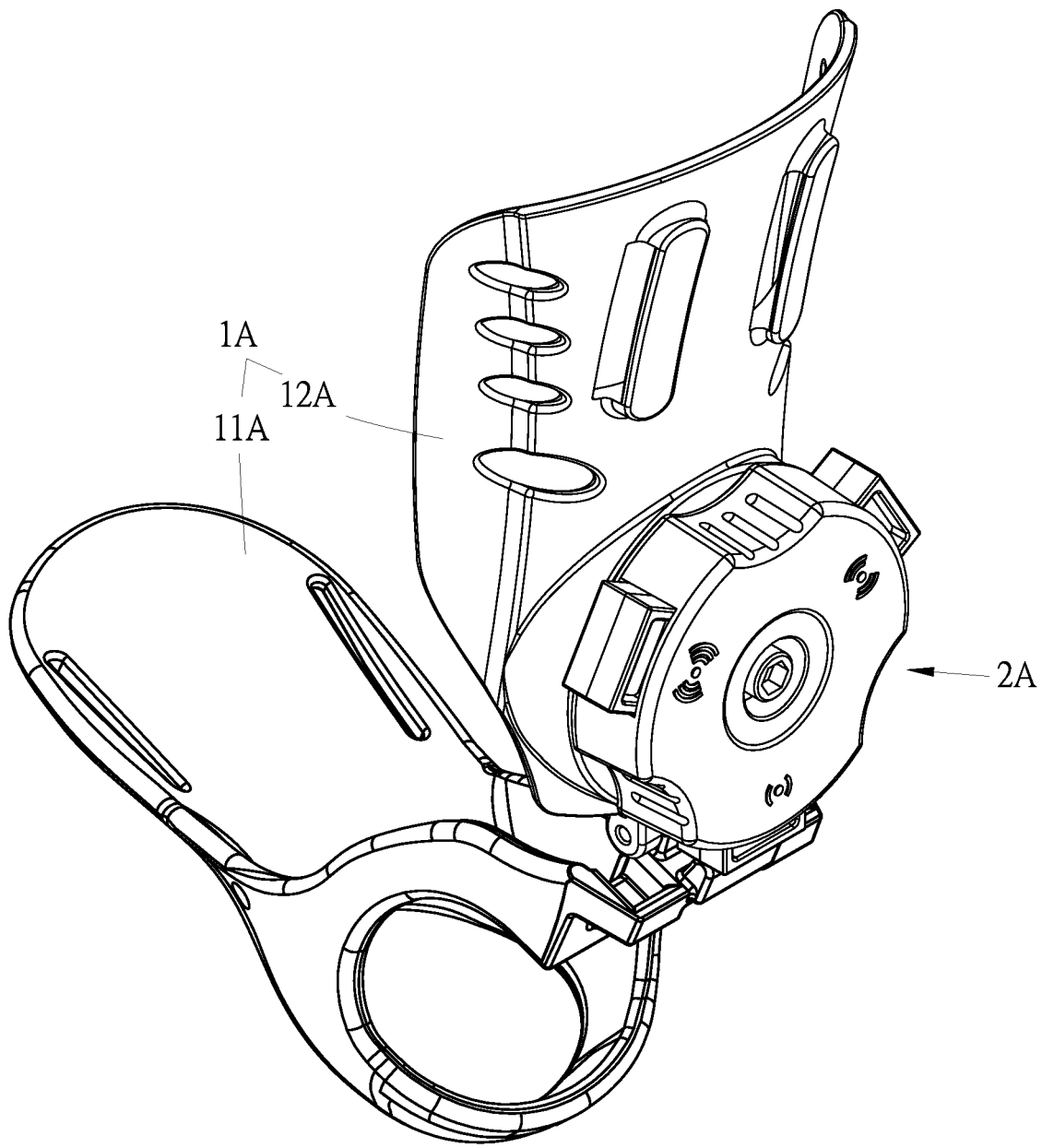
FIG. 13 is the three-dimensional outside view of another embodiment of the present invention.
Figure 14:
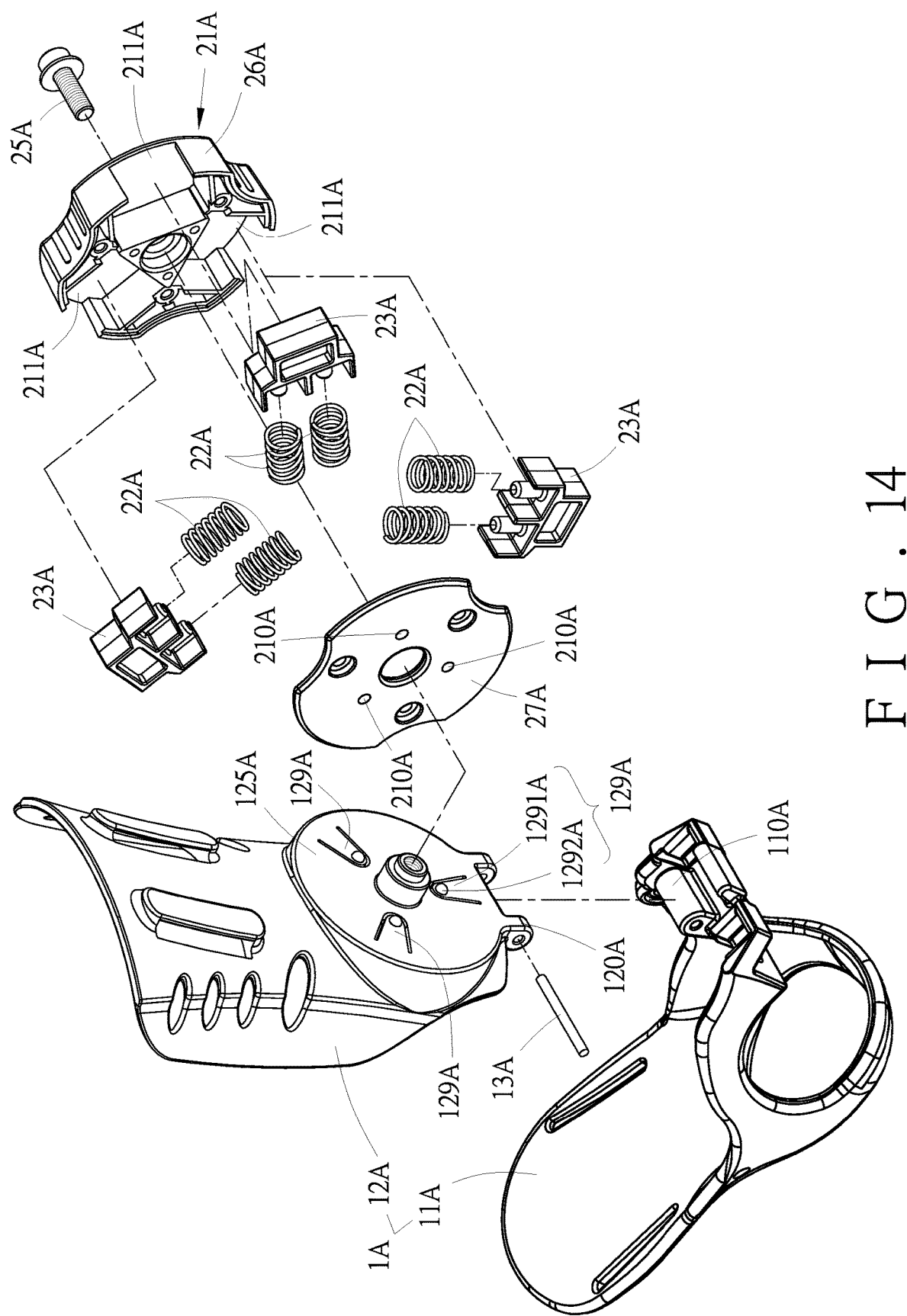
FIG. 14 is the three-dimensional exploded view of another embodiment of the present invention.

FIGS. 13 and 14 show another embodiment of the present invention, there is also an assistive device body (1A). The assistive device body (1A) comprises a foot support base (11A) and a brace (12A). The foot support base (11A) is movably connected to the brace (12A). For example, the foot support base (11A) and the brace (12A) have a pivot joint part (110A)(120A) corresponding to each other. The pivot joint part (110A) of the foot support base (11A) can be pivoted on the pivot joint part (120A) of the brace (12A) by a pivot (13A), so that the foot support base (11) and the brace (12) can pivot on each other. The main difference to previous embodiment is that the elastic module mounting part (125A) of the brace (12A) is for mounting different forms of elastic module (2A).

Figure 15:
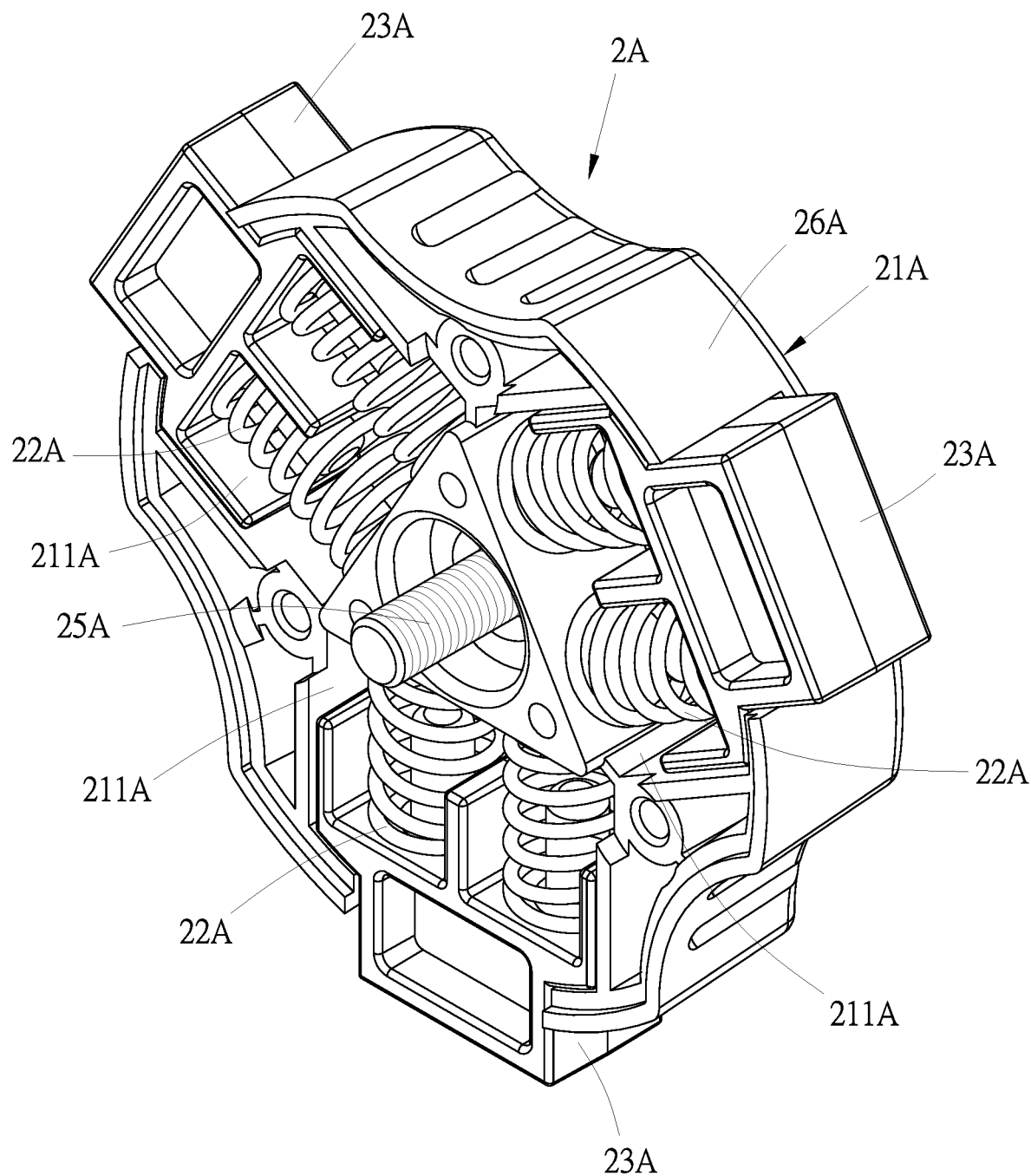
FIG. 15 is the three-dimensional outside view of elastic module without base in another embodiment of the present invention.

As shown in FIGS. 14 and 15, to be specific, the elastic module (2A) comprises a casing holder (21A), a plurality of springs (22A) and a plurality of push-prop pieces (23A). The casing holder (21A) is pivoted on the elastic module mounting part (125A) by a pivot (25A). A top cap (26A) of the casing holder (21A) is surrounded with a plurality of holding chambers (211A) centered on the pivot (25A). Each of said holding chambers (211A) is provided with one of the springs (22A) and one of the push-prop pieces (23A). One of the elastic module mounting part (125A) and the casing holder (21A) has a plurality of snaps. The snaps (129A), for example, can be distributed on the elastic module mounting part (125A) annularly centered on the pivot (25A). Each snap (129A) is formed by a cantilevered member (1291A) having a projection (1292A) at its distal end. The other one of the casing holder (21A) and the elastic module mounting part (125A) has a plurality of clamping holes. The clamping holes (210A), for example, can be distributed on a base (27A) of the casing holder (21A) annularly centered on the pivot (25A), so that the projections (1292A) of the snaps (129A) can engage with a corresponding one of the clamping holes (210A).

Figure 16:
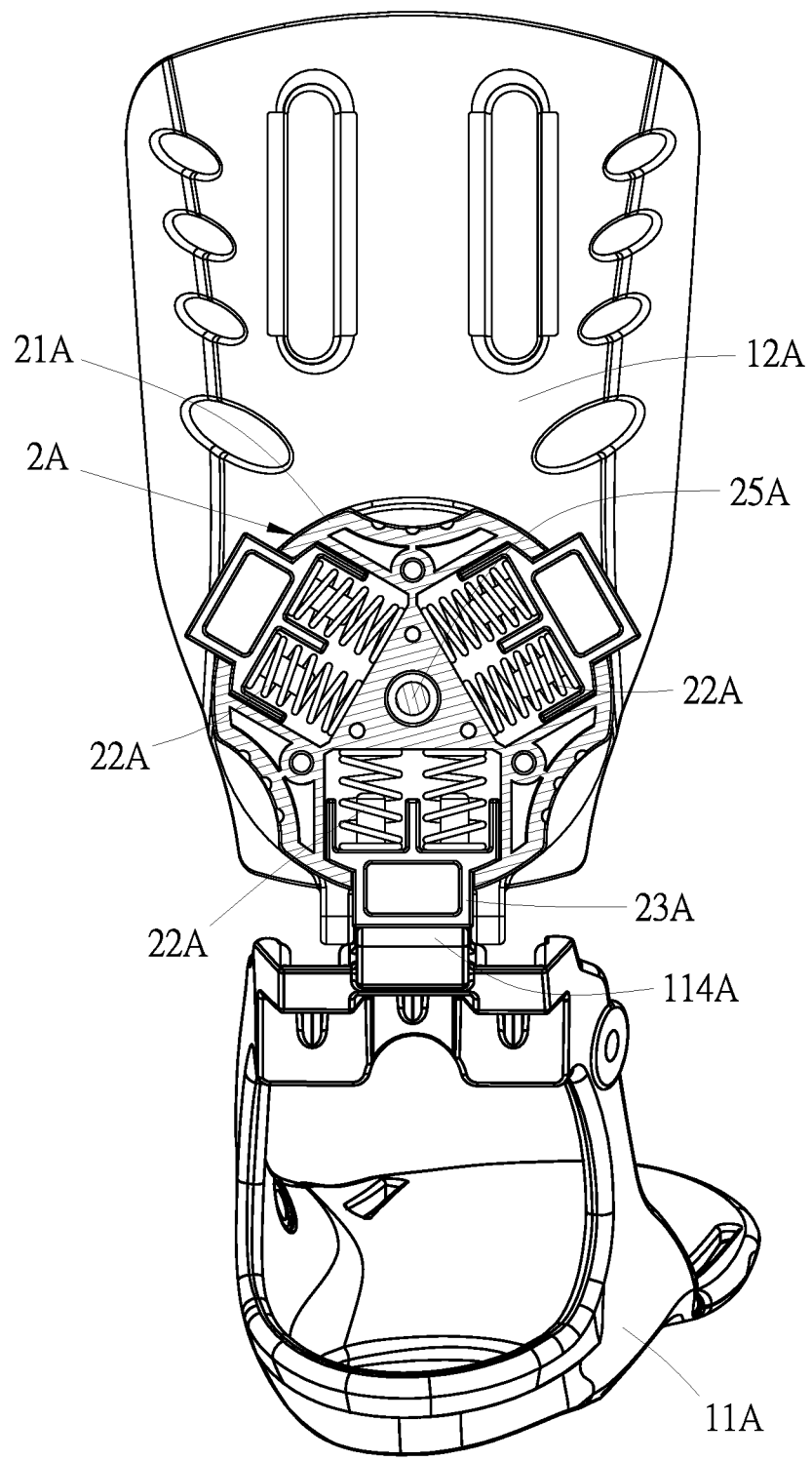
FIG. 16 is the rear view and partial section view of another embodiment of the present invention.
Figure 17:
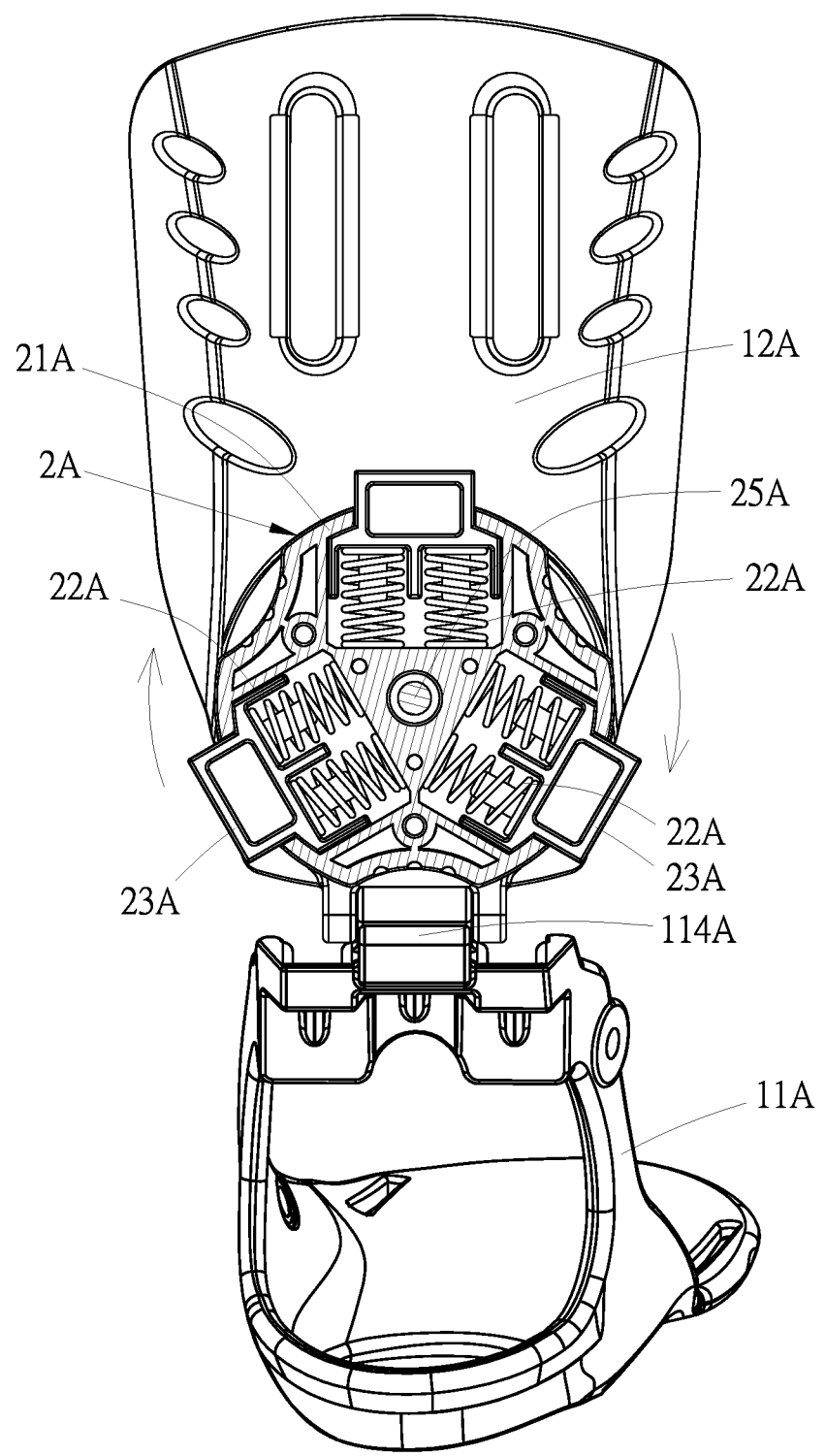
FIG. 17 is the rear view and partial section view of turning elastic module in another embodiment of the present invention.

FIGS. 16 and 17 show the service condition. When the elastic force of springs (22A) is too strong or too weak, the user's gait mismatches normal gait or is uncomfortable, or when the springs (22A) shall be changed, the user can press said push-prop pieces (23A) to disengage the push-prop pieces (23A) from the propping part (114A) of the foot support base (11A). As shown in FIG. 17 and FIG. 14, the casing holder (21A) is turned to disengage the clamping holes (210A) of the casing holder (21A) from the projections (1292A) of the snaps (129A), so that the casing holder (21A) pivots on the brace (12A) centering on the pivot (25A). Afterwards, the other clamping holes (210A) of the casing holder (21A) engage with the projections (1292A) of the snaps (129A), so that the other push-prop pieces (23A) prop the propping part (114A) of the foot support base (11A). Thereby, the springs (22A) of different E-moduli or new springs (22A) can be mounted without dismounting the whole elastic module (2A), so as to enhance the convenience of product use.

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims.

What is claimed is:

1. A foot assistive device for improving drop foot gait, comprising:
    an assistive device body including a foot support base and a brace, the foot support base is movably connected to the brace, and the brace includes an elastic module mounting part; and
    an elastic module coupled to both the foot support base and to the brace, the elastic module being releasably coupled to the elastic module mounting part; the elastic module including a casing holder and at least one spring disposed in a holding space thereof, and wherein a preset support included angle is formed between the foot support base and the brace responsive to an elastic force of the spring; the preset support included angle is less than 90°;

wherein one of the casing holder and the elastic module mounting part includes a snap, and the other one of the casing holder and the elastic module mounting part includes a clamping hole, the snap being defined by a cantilevered member having a projection at a distal end thereof for releasable engagement with the clamping hole, and the elastic module being removable from the elastic module mounting part responsive to displacement of the projection of the cantilevered member from the clamping hole.

2. The device defined in claim 1, wherein both of the foot support base and the brace have a pivot joint part, the pivot joint part of the foot support base is pivoted on the pivot joint part of the brace.

3. The device defined in claim 2, wherein the elastic module mounting part is located near the pivot joint part of the brace.

4. The device defined in claim 1, wherein the casing holder has an opening, the opening is connected to the holding space; the elastic module has at least one push-prop piece, the at least one push-prop piece is movably connected to the casing holder and located at the opening; the at least one spring props the at least one push-prop piece, the at least one push-prop piece thereby props a propping part of the foot support base.

5. The device defined in claim 4, wherein the casing holder has an elongated slot; the elastic module has a latch through the elongated slot and the at least one push-prop piece to thereby limit displacement of the at least one push-prop piece.

6. The device defined in claim 2, wherein the foot support base has a hollow heel restraining part, the heel restraining part is located near the pivot joint part of the foot support base.

7. The device defined in claim 6, wherein the foot support base has two first bandage connecting parts, a second bandage connecting part, and a third bandage connecting part; said two first bandage connecting parts are opposite to each other, and said two first bandage connecting parts are located adjacent a front end of the foot support base; the second bandage connecting part is located adjacent a back end of the foot support base; the third bandage connecting part is located between the second bandage connecting part and the back end, and the third bandage connecting part is positioned higher than the second bandage connecting part.

8. The device defined in claim 7, wherein the brace has two fourth bandage connecting parts; said two fourth bandage connecting parts are opposite to each other, and said two fourth bandage connecting parts are located adjacent a top of the brace.

9. The device defined in claim 8, wherein a leg contact side of the brace is provided with a soft protection pad.

10. The device defined in claim 2, the elastic module mounting part is located near the pivot joint part of the brace; the elastic module has a plurality of push-prop pieces; the at least one spring is further a plurality of springs; the casing holder is pivoted on the elastic module mounting part by a pivot; the casing holder is surrounded with a plurality of holding chambers centered on the pivot; each of said holding chambers is provided with one of said plurality of springs and one of said plurality of push-prop pieces; when the casing holder is turned, one of said plurality of push-prop pieces props a propping part of the foot support base.

11. The device defined in claim 10, wherein a plurality of said snaps and said clamping holes are distributed annularly centering on the pivot.

* * * * *